(12) United States Patent
Mirarchi

(10) Patent No.: US 6,494,894 B2
(45) Date of Patent: Dec. 17, 2002

(54) COATED WIRE

(75) Inventor: Thomas F. Mirarchi, Shrewsbury, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/809,344

(22) Filed: Mar. 15, 2001

(65) Prior Publication Data

US 2001/0037125 A1 Nov. 1, 2001

Related U.S. Application Data

(60) Provisional application No. 60/189,921, filed on Mar. 16, 2000.

(51) Int. Cl.$^7$ ............................................... A61B 17/00
(52) U.S. Cl. ........................... 606/190; 604/94; 604/95; 128/772
(58) Field of Search ................................. 128/772, 657; 604/95, 164, 283, 170, 180, 280, 281, 282; 600/585, 433, 434; 606/190

(56) References Cited

U.S. PATENT DOCUMENTS

| | | |
|---|---|---|
| 4,724,846 A | 2/1988 | Evans |
| 4,790,831 A | 12/1988 | Skribiski |
| 4,925,445 A | 5/1990 | Sakamoto et al. |
| 4,932,419 A | 6/1990 | De Toledo |
| 5,054,501 A | 10/1991 | Chuttani et al. |
| 5,147,317 A | 9/1992 | Shank et al. ................. 604/164 |
| 5,213,111 A | 5/1993 | Cook |
| 5,228,453 A | 7/1993 | Sepetka |
| 5,282,478 A | 2/1994 | Fleishhaker, Jr. et al. |
| 5,299,580 A | 4/1994 | Atkinson et al. |
| 5,333,620 A | 8/1994 | Moutafis et al. |
| 5,365,942 A | 11/1994 | Shank |
| 5,377,690 A | 1/1995 | Berthiaume |
| 5,379,779 A | 1/1995 | Rowland et al. |
| 5,405,338 A | 4/1995 | Kranys |
| 5,433,200 A | 7/1995 | Fleischhacker, Jr. ........ 128/657 |
| 5,498,250 A | 3/1996 | Prather |
| 5,640,970 A | 6/1997 | Arenas |
| 5,722,424 A | 3/1998 | Engelson |
| 5,827,201 A | 10/1998 | Samson et al. |
| 5,840,046 A | 11/1998 | Deem |
| 5,910,364 A | 6/1999 | Miyata et al. |
| 5,924,998 A | 7/1999 | Cornelius et al. |
| 5,951,494 A | 9/1999 | Wang et al. |
| 6,019,737 A | 2/2000 | Murata |
| 6,251,085 B1 | 6/2001 | Tezuka |
| 6,306,105 B1 | 10/2001 | Rooney et al. |

FOREIGN PATENT DOCUMENTS

| | | |
|---|---|---|
| EP | 0 820 782 A2 | 7/1997 |
| EP | 0 826 389 A2 | 8/1997 |
| EP | 0 868 924 A2 | 4/1998 |
| WO | WO 98/39049 | 3/1998 |

*Primary Examiner*—John J. Calvert
*Assistant Examiner*—Robert H. Muromoto, Jr.
(74) *Attorney, Agent, or Firm*—Crompton, Seager & Tufte LLC

(57) ABSTRACT

A coated wire for medical applications including a length of biocompatible wire material. The wire material can be coated along a portion of the perimeter of the wire. The deposition of the coating can cover less than the total circumference of the wire.

32 Claims, 2 Drawing Sheets

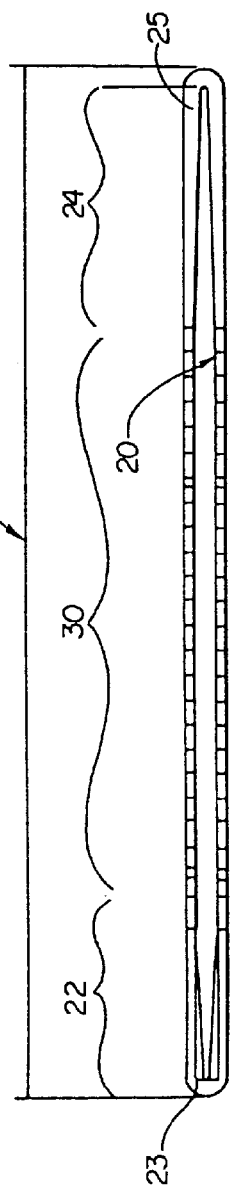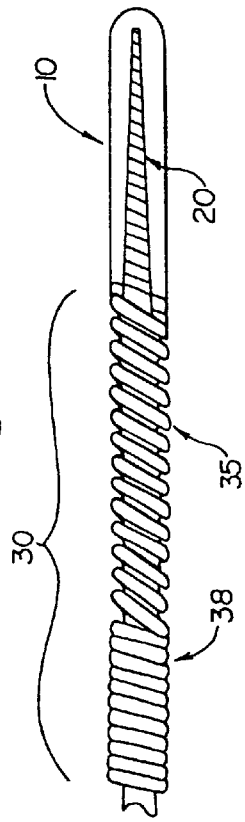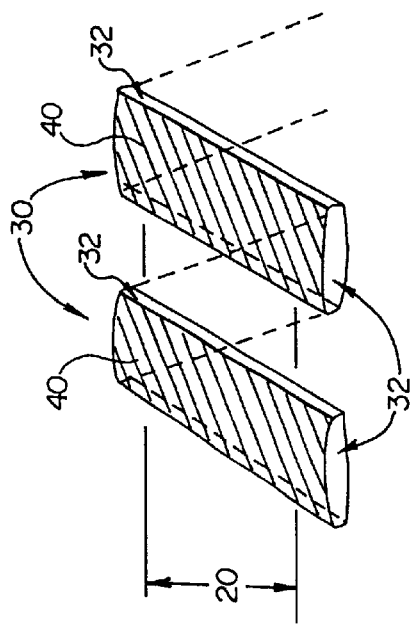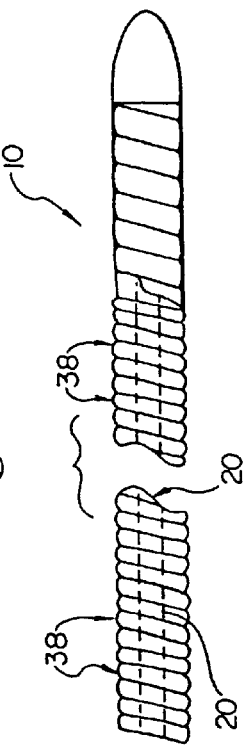
Fig. 1
Fig. 2
Fig. 7
Fig. 3

COATED WIRE

CROSS REFERENCE TO RELATED APPLICATION

This application claims the benefit of U.S. Provisional Application Ser. No. 60/189,921, filed on Mar. 16, 2000.

FIELD OF THE INVENTION

The present invention relates to the medical field of intraluminal wires used to access distal areas of the body. Specifically, the present invention relates to wires partially coated with a lubricious material. The coated wire may be used to construct a guide wire with a central core and surrounded by the coated wire coiled around the core. Alternatively, the partially coated wire may be used to construct a variety of devices including baskets, snares, laparoscopic instruments or small coils that may be used within numerous medical specialties, including cardiology, urology, and radiology.

BACKGROUND OF THE INVENTION

Minimally invasive medical procedures can be performed at remote sites by inserting and navigating endoscopic equipment into and through blood vessels or body lumens to the treatment site. A specific site may be difficult to reach for many reasons including vessel or tract tortuosity, lumen constriction e.g. edema or tumor impingement or lumen blockage e.g. ureterolithiasis.

Insertion of a guide wire can facilitate access to the treatment site. Catheters or medical tools can then be advanced over the guide wire to the specific site. To achieve accurate placement the guide wire should incorporate the somewhat competing features of pushability, kink resistance, torqueability and bendability. Guide wire designs known in the art to meet these criteria include a guide wire design characterized by a solid metal core surrounded by a metal coil. Metals for the core may include spring steels, stainless steels and NiTi alloys. The same variety of metals used as core materials can be used for the coil wire, including stainless steel or NiTi alloys such as NITINOL wire. The coil wire may be round wire or flat wire; the coil wire may be made of a single wire strand or may be made of multifilar wire. The coil wire may wrap around the entire length of the core or only a portion of the core. The adjacent turns of the coil wire may or may not be tightly wrapped with succeeding turns of the coil wire touching, the coil wire may be wrapped around the core in an open fashion, or the core may be surrounded by coil wire that is tightly wrapped along a portion of the core and open wrapped along a subsequent portion of the core. The coil can be, but need not be, in axial compression.

Important to smooth advancement and retraction of the guide wire is an exterior surface of the guide wire that creates minimal friction between the inner wall of the vasculature or body lumen and the exterior surface of the guide wire. Similarly, to advance catheters or other equipment over or along a guide wire, a balance is required between ease of movement of the catheter or equipment along the guide wire and retention of the desired positioning of the guide wire at the treatment site.

Guide wire construction typically includes use of a pre-coated coil wire to minimize friction between the external surface of the guide wire and the inner wall of the bodily lumen or medical equipment. The guide wire could, however, be spray coated after assembly to increase lubricity.

Circumferential coating of the wire coil may interfere with or prevent desired bonding (including adhesive, weld, and solder) between the coil wire and core. Abrasion between adjacent coated coils of the coil wire may result in flaking or sloughing of coating material. Abraded particles of coating material could enter the vascular or body lumen.

Construction and use requirements of various other coated medical wires and endoscopic instruments, such as urology baskets and snares, laparoscopic instruments or radiology coils may mimic the construction and use requirements of a coated guide wire.

SUMMARY OF THE INVENTION

The invention pertains to a wire partially coated with a lubricious material. The present invention provides benefits over the prior art by providing a wire that is coated only along a portion of the wire perimeter. The lubricious coating is deposited on the wire along the exterior perimeter portion of the wire that could have direct contact with either an internal body lumen or an inner lumen of a catheter. Lubricious materials for coating select portions of the wire include PTFE and hydrophilic materials such as HYDROPASS or GLIDEX. A single material may be coated along the selected portion of the wire, or different materials may be applied along different segments of the wire.

The uncoated portions of the wire provide surfaces for bonding to other materials that are preferably free of interference from the coating material. For example, guide wire construction may require bonding between a wire core and wire coil surrounding the core. The uncoated portions of the coil wire provide a surface preferably free from a coating material; such uncoated portion may more readily enhance bonding between the core and the coil wire.

If the partially coated wire is formed into a coil configuration, such as may occur in construction of a guide wire, where interstices of the coils are preferably uncoated, the potential for coating material flake-off or rub-off resulting from abrasion between adjacent turns of the coiled wire is reduced or eliminated.

BRIEF DESCRIPTION OF THE DRAWINGS

FIG. 1 is a longitudinal section of an embodiment of a guide wire assembly consisting of a wire core surrounded by a coated coil wire;

FIG. 2 is a longitudinal section of a guide wire assembly depicting the wire core wrapped by a coil wire in both an open fashion and a tightly wrapped manner;

FIG. 3 is a longitudinal section of a guide wire assembly depicting the wire core tightly wrapped by the coil wire;

FIG. 7 is a representation of the winding of a coil wire around the core wire;

DETAILED DESCRIPTION OF THE INVENTION

Figure 4:
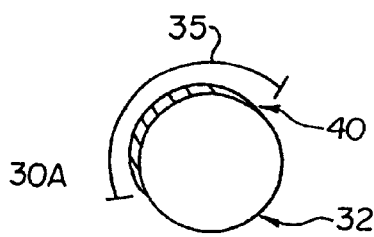
FIG. 4 is a cross section of a partially coated round coil wire.

The following description references the drawings in which like elements in different drawings are identically numbered. The drawings depict selected embodiments and are not intended to limit the scope of the invention.

FIG. 1 shows an embodiment of the guide wire 10. The dimensions of the guide wire 10 and the core 20 will vary depending on the medical application. The distal portion 22 of core 20 may be tapered, as shown, to provide flexibility to guide wire 10.

Core 20 may be formed of spring steels, stainless steel, super-elastic materials such as the NiTi alloys e.g. NITINOL, linear-elastic materials or other biocompatible materials.

Surrounding core 20 is coil wire 30. Coil wire over wire core is well known in the guide wire art and is described in detail in U.S. Pat. No. 5,147,317 to Shank which is incorporated by reference. Coil wire 40 may be made of a variety of metallic materials including super-elastic or linear-elastic materials such as NiTi alloy or NITINOL, conventional stainless steel alloys such as 304V, or 361L.

Coil wire 30 is wrapped around some portion of the length of core 20. In one embodiment, as depicted in FIG. 1, the coil wire is wrapped around a central portion of the core; the proximal portion 22 and tapered distal portion 24 of the core may be surrounded by polymer tips, 23 and 25 respectively.

Figure 5:
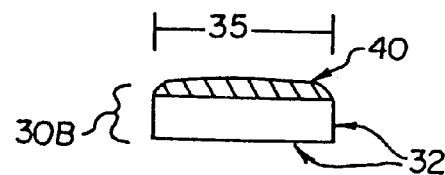
FIG. 5 is a cross section of a partially coated flat coil wire.

Coil wire 30 may be formed of round wire as depicted in cross-section in FIG. 4 or formed of flat ribbon wire as depicted in cross-section in FIG. 5. The flat ribbon wire can be formed by, for example, rolling a round cross sectional wire. The transverse ends of the cross section of the ribbon wire can be rounded or with subsequent processing squared. It can be appreciated that numerous cross sectional shapes can be used in accordance with the present invention. Or, coil 30 may be formed of cross-wound multifilar (as described in U.S. Pat. No. 4,932,419 to de Toledo which is incorporated herein by reference) or multifilar single coil wire.

Coil wire 30 is wrapped in a helical fashion about core 20. The pitch chosen to wind the coil wire 30 may be determined by the particular application and flexibility requirements for the guide wire 10.

The pitch can vary from tightly wrapped so that each turn touches the preceding turn or the pitch may be such that coil wire 30 is wrapped about core 20 in an open fashion so that there is space between each succeeding turn of the coil wire.

FIG. 2 demonstrates an open fashion of wrapping the coil wire 30. Succeeding wraps 35 of coil wire 30 do not overlap or touch the preceding wrap.

FIG. 2 and FIG. 3 demonstrate sections of coil 30 which are tightly wrapped so that succeeding turns 38 of coil wire 30 touch preceding turns 38 of coil wire 30. As depicted in FIG. 2, in one embodiment the pitch of coil wire 30 varies along the distance of core wire 20, providing variable flexibility along the length of guide wire 10.

FIGS. 4 and 5 illustrate, in cross section of a round coil wire 30A, and a flat coil wire 30B, application of a lubricious coating 40 along an exterior portion 35 of the perimeter of the coil wire 30A or 30B. The remaining portion 32 of the perimeter of the coil wire is preferably uncoated. Lubricious materials for coating the coil wire 30 can include hydrophobic materials such as PTFE and silicon, and hydrophilic materials such as HYDROPASS.

Methods for selectively coating the coil wire 30 include masking wire segment 32 prior to application of the coating material 40 along the wire segment 35 selected for coating. Alternatively, the coating material 40 may be applied onto the select segment 35 by dipping a portion of the wire into the coating material or by spraying the coating material onto selected portions of the wire. Other methods for selectively coating a wire include rolling the material onto the wire. Transfer methods in the coating and printing arts may also be used to selectively coat the wire.

Figure 6:
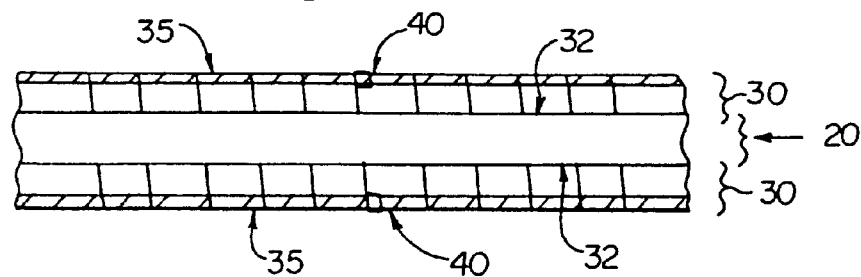
FIG. 6 is an expanded view of a portion of a longitudinal section of a guide wire assembly consisting of a wire core surrounded by a coated coil wire.

The longitudinal section of the guide wire 20 shows in FIG. 6 the outer disposition 40 of the coating on the coil wire 30. The coil wire 30 interface 32 with the core wire 20 is preferably free of lubricious coating.

An exploded longitudinal view of an open wrapped coil wire in FIG. 7 shows the application of the coating 40 along the external surface of coil wire 30; edges 32 and the lower surface of coil wire 30 are preferably uncoated. Abrasion from surface-to-surface interface between consecutive turns of coil wire 30 are unlikely to result in chipping or flaking the coating 40 since these interfaces are preferably free of any coating.

Figure 8:
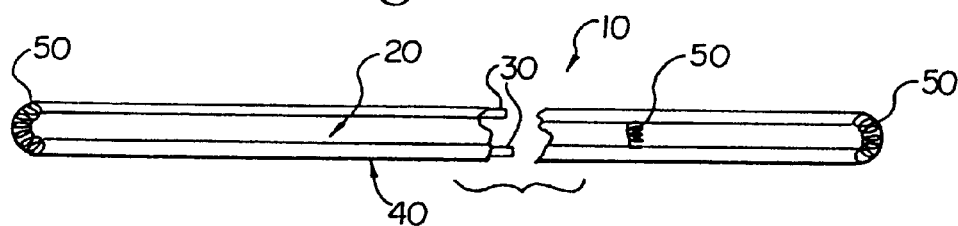
FIG. 8 is a longitudinal section of a guide wire assembly in which the coil wire is bonded with adhesive to the core wire.
Figure 9:
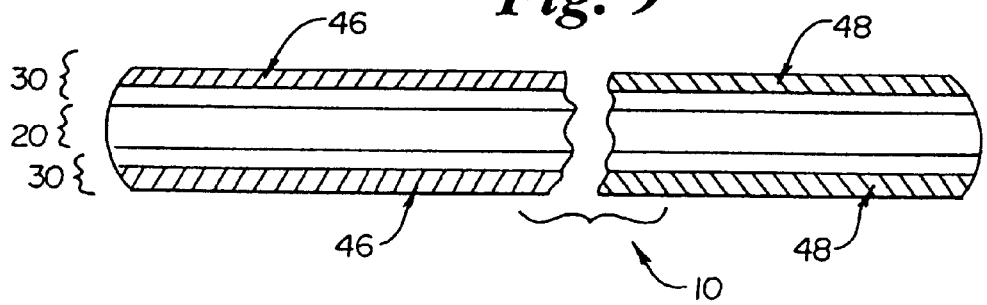
FIG. 9 depicts use of two different lubricious coatings to pre-coat the coil wire.

Bonding core wire 20 to coil wire 30 may provide improved torque transmission of guide wire 10. Coil wire 30 may be bonded to core wire 20 along the length of core wire 20 or in discrete sections. Adhesive bonding, swaging, brazing, soldering or welding are among the alternatives to bond the coil wire 30 to the core wire 20. Plating or etching is usually not required to prepare the core wire 20 surface since the coil wire bonding surface 32 is preferably uncoated. Alternately, specialty platings may be applied to enhance adhesion of the coating to the wire, or enhanced biocompatibility of the uncoated surface in the presence of body fluids. This is especially advantageous when the core wire 20 and coil wire 30 are materials that are difficult to weld together; adhesive bonding 50 offers a potential solution. FIG. 8 shows adhesive bonds 50 in areas that could previously have required spot welds or ball welds.

An alternative guide wire 10 construction includes the use of different lubricious coatings along the surface of the coil wire 30. In one alternative, the proximal segment of the core wire 20 may be wound with Teflon coated 46 coil wire 30; the distal segment of the core wire 20 may be wound with a hydrophilic material such as HYDROPASS coated 48 coil wire 30.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A partially coated guidewire, comprising:
   an elongate core member;
   a coil including a wire coupled to at least a portion of the core member, the coil having an exterior portion and an interface portion located where the coil interfaces with the core member; and
   a coating disposed along at least a portion of the exterior portion of the coil;
   wherein the disposition of the coating is less than the perimeter of the wire.

2. The coated guidewire in accordance with claim 1, wherein the core member includes a tapered distal portion.

3. The coated guidewire in accordance with claim 1, wherein the core member is comprised of a super elastic alloy.

4. The coated guidewire in accordance with claim 1 wherein the coil comprises a round wire.

5. The coated guidewire in accordance with claim 1, wherein the coil comprises a flat ribbon.

6. The coated guidewire in accordance with claim 1, wherein the coil has an open pitch.

7. The coated guidewire in accordance with claim 1, wherein the coil has a tightly wrapped pitch.

8. The coated guidewire in accordance with claim 1, wherein the coating is comprised of polytetrafluoroethylene.

9. The coated guidewire in accordance with claim 1, wherein the coating is comprised of silicon.

10. A coated guidewire, comprising:

a core member;

a coil encircling at least a portion of the core member, the coil having an exterior portion adapted for contact with the inner lumen of a cavity, an interface portion that is adapted and configured to be fixedly coupled to the core member, and a side portion that faces a succeeding turn of the coil;

wherein the exterior portion includes a lubricious coating, and wherein the interface portion and the side portion are free from the coating.

11. The coated guidewire in accordance with claim 10, wherein the core member includes a tapered distal portion.

12. The coated guidewire in accordance with claim 10, wherein the core member is comprised of a super elastic alloy.

13. The coated guidewire in accordance with claim 10, wherein the coil comprises a round wire.

14. The coated guidewire in accordance with claim 10, wherein the coil comprises a flat ribbon.

15. The coated guidewire in accordance with claim 10, wherein the coil has an open pitch.

16. The coated guidewire in accordance with claim 10, wherein the coil has a tightly wrapped pitch.

17. The coated guidewire in accordance with claim 10, wherein the coating is comprised of polytetrafluoroethylene.

18. The coated guidewire in accordance with claim 10, wherein the coating is comprised of silicon.

19. A method for coating a guidewire, comprising the steps of:

providing a core member;

coupling a coil to at least a portion of the core member, the coil having an exterior portion and an interface portion that interfaces with the core member; and coating the exterior portion of the coil with a coating material;

wherein the step of coupling a coil to at least a portion of the core member includes encircling the core member with the coil, wherein the coil encircles the core member at a pitch that defines a side coil region between succeeding turns of the coil, and wherein the side coil region is free of the coating.

20. The method in accordance with claim 19, wherein the step of coupling a coil to at least a portion of the core member includes encircling the core member with the coil, wherein the coil encircles the core member in an open pitch that defines a side coil region between succeeding turns of the coil, and wherein the side coil region is free of the coating.

21. The method in accordance with claim 19, wherein the step of coupling a coil to at least a portion of the core member includes encircling the core member with the coil, wherein the coil encircles the core member in a tightly wrapped pitch that defines a side coil region between succeeding turns of the coil, and wherein the side coil region is free of the coating.

22. The method in accordance with claim 19, wherein the step of coating the exterior portion of the coil with a coating material includes dipping a portion of the coil into the coating material.

23. The method in accordance with claim 19, wherein the step of coating the exterior portion of the coil with a coating material includes spraying the coating material onto the coil.

24. The method in accordance with claim 19, wherein the step of coating the exterior portion of the coil with a coating material includes rolling the coating material onto the coil.

25. The method in accordance with claim 19, further comprising the step of bonding the coil to the core member.

26. The method in accordance with claim 25, wherein the step of bonding the coil to the core member includes adhesive bonding.

27. The method in accordance with claim 25, wherein the step of bonding the coil to the core member includes swaging.

28. The method in accordance with claim 25, wherein the step of bonding the coil to the core member includes brazing.

29. The method in accordance with claim 25, wherein the step of bonding the coil to the core member includes soldering.

30. The method in accordance with claim 25, wherein the step of bonding the coil to the core member includes welding.

31. The method in accordance with claim 19, wherein the pitch is an open pitch.

32. The method in accordance with claim 19, wherein the pitch is a tightly wrapped pitch.

* * * * *